(12) United States Patent
Rubio

(10) Patent No.: US 7,581,267 B2
(45) Date of Patent: Sep. 1, 2009

(54) METHOD OF USING A SIDE SLEEPING PILLOW

(76) Inventor: Horacio C. Rubio, P.O. Box 534131, Harlingen, TX (US) 78553

(*) Notice: Subject to any disclaimer, the term of this patent is extended or adjusted under 35 U.S.C. 154(b) by 51 days.

(21) Appl. No.: 11/985,795

(22) Filed: Nov. 16, 2007

(65) Prior Publication Data
US 2008/0066235 A1 Mar. 20, 2008

Related U.S. Application Data

(62) Division of application No. 11/353,801, filed on Feb. 13, 2006, now abandoned.

(60) Provisional application No. 60/652,131, filed on Feb. 11, 2005.

(51) Int. Cl.
*A47C 20/00* (2006.01)

(52) U.S. Cl. .................. 5/636; 5/646; 5/632

(58) Field of Classification Search ........ 5/632, 5/646, 636, 648; D6/601
See application file for complete search history.

(56) References Cited

U.S. PATENT DOCUMENTS

| | | | | | |
|---|---|---|---|---|---|
| 4,074,376 | A | * | 2/1978 | Bond | 5/632 |
| 4,118,813 | A | * | 10/1978 | Armstrong | 5/638 |
| 4,850,067 | A | * | 7/1989 | Latorre | 5/636 |
| 5,457,832 | A | * | 10/1995 | Tatum | 5/636 |
| 5,479,667 | A | * | 1/1996 | Nelson et al. | 5/636 |
| 6,226,817 | B1 | | 5/2001 | Rubio | |
| 6,957,497 | B2 | * | 10/2005 | Greenawalt et al. | 33/512 |

* cited by examiner

*Primary Examiner*—Peter M. Cuomo
*Assistant Examiner*—William Kelleher

(57) ABSTRACT

A pillow is shaped to encourage a sleeper to sleep on a side, rather than on the back. This is accomplished by providing a pair of arms extending forwardly from a head support. The arms are spaced apart less than the width of the sleeper's shoulders so it is uncomfortable for the sleeper to roll over onto the back. The arms are spaced from the edges of the pillow to provide for a side ramp, inclined upwardly toward the head support, to receive the forearm of the sleeper.

2 Claims, 1 Drawing Sheet

METHOD OF USING A SIDE SLEEPING PILLOW

This application is based on provisional application Ser. No. 60/652,131, filed Feb. 11, 2005 now abandoned, for which priority is claimed and is a division of application Ser. No. 11/353,801, filed Feb. 13, 2006.

This invention relates to a method of using a pillow designed to keep an individual from sleeping on the back, i.e. it is designed to keep an individual sleeping on one side or the other.

BACKGROUND OF THE INVENTION

Many individuals experience sleeping disorders and one in particular is a snoring condition known as Obstructive Sleep Apnea (OSA). OSA has been reported by the National Sleep Foundation to affect approximately 71 million people at least a few times a week. It is caused usually by the person's airway narrowing in the upper track. Many factors can contribute to this problem, but generally decreased muscle tone and fatty deposits in the throat are blamed. It is generally believed that elevating a person's head and sleeping on the side can reduce or eliminate this snoring problem, hence a better night's sleep.

One archaic treatment is for the snorer to wear a tee shirt having a tennis ball sewn in the back, the idea being that when the sleeper is on the back, the tennis ball will ultimately cause discomfort whereupon the sleeper will roll onto the side. This is supposed to keep the sleeper on the side but being awaken in order to roll onto the side is not very restful.

Disclosures relevant to this invention are found in U.S. Pat. Nos. 4,850,067; 5,479,667 and 6,226,817.

SUMMARY OF THE INVENTION

In this invention, a pillow is provided that encourages a sleeper to stay on one side by making it difficult to roll over onto the back. Thus, this pillow construction does what medical professionals desire but with a more comfortable result and minimum disturbance to the sleeper and a happier bedmate.

This is accomplished by providing a pillow that is too narrow for the user to sleep on their back and is based on the observation that most people are wider from side-to-side than from front-to-back. The pillow accordingly has arms, abutments or side panels that are narrower than the sleeper's back. Thus, the only position the sleeper can normally assume is on one side.

In one embodiment, the pillow has a wedge shaped design providing a center section to receive an individual in a side sleeping position and two spaced arms or fixed blocks not permitting the individual to move onto their back. The sleeper's head rests on an elevated portion thereby allowing the shoulder to be received in a comfortable manner in a slot formed by the pillow of this invention. The sleeper's face is supported either with the elevated head rest or on the arm/block extension area, depending on the sleeper's preference, as when the user sleeps in a curled side position. Preferably, both sides of the pillow of this invention provides a side ramp to allow an arm to rest in a side sleeping position without interfering with the torso.

For a greater elevation or angle, one or more additional wedges may be provided, to be added underneath the main center section of the pillow. In the alternative, a mechanical arrangement may be provided to increase the inclination of the pillow.

It is an object of this invention to provide an improved pillow promoting a user to sleep on a side and method of using the same.

Another object of this invention is to provide a side sleeping pillow including a side ramp for receiving the arm of the sleeper and method of using the same.

These and other objects and advantages of this invention will become more apparent as this description proceeds, reference being made to the accompanying drawings and appended claims.

DETAILED DESCRIPTION

Figure 1:
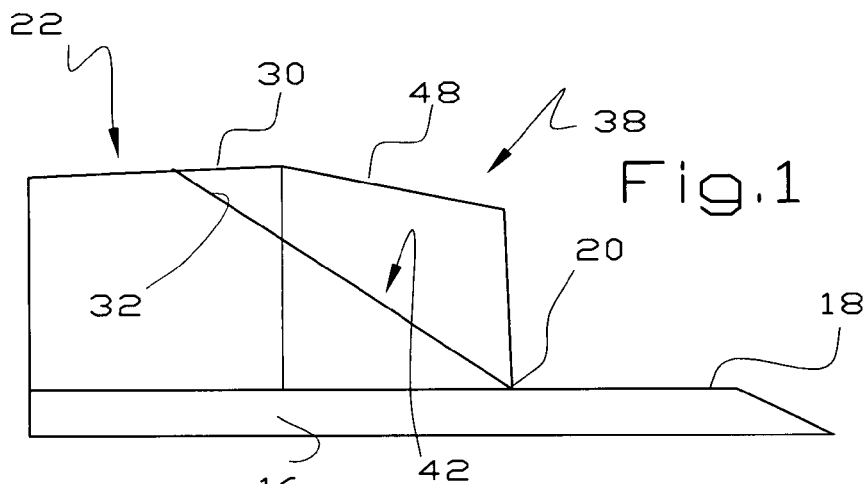
FIG. 1 is an isometric view of the pillow of this invention, illustrated without an overlying cover in order to show its internal construction.
Figure 2:
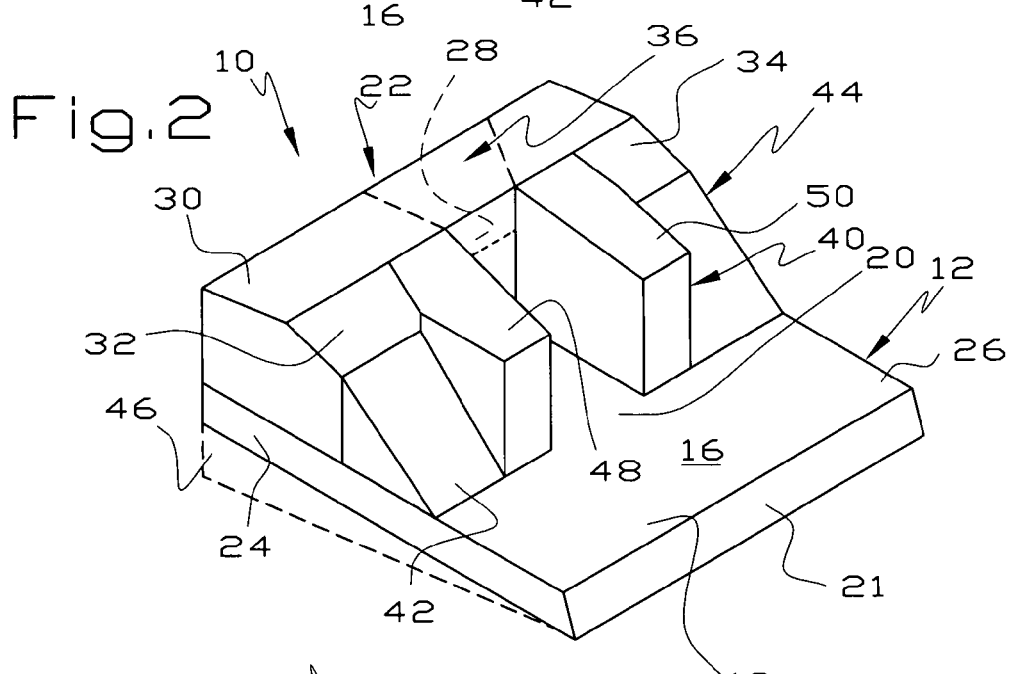
FIG. 2 is a side view of the inner core of the pillow of FIG. 1.
Figure 3:
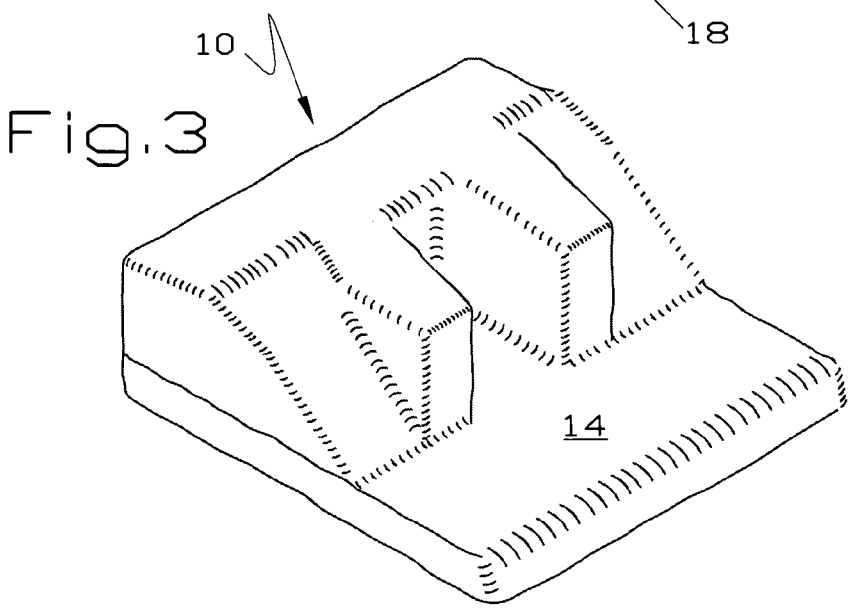
FIG. 3 is an isometric view of the pillow of FIG. 1 to which has been added an external cover.

Referring to FIGS. 1-3, there is illustrated a pillow 10 having an internal core 12 which may be slightly compressible foam, an inflatable member or the like, and a cover 14 of a suitable finish material, such as a soft foam sheet. The core 12 includes a generally horizontal planar rectangular base 16 which provides a waist and lumbar support assembly 18 and a thoracic support assembly 20. The waist and lumbar support assembly 18 includes a leading edge 21 of elongate wedge shape to merge smoothly with an underlying bed surface.

A head support assembly 22 extends generally perpendicularly upwardly from the base 16 and extends laterally to adjacent the sides 24, 26 of the base 16. Although the base 16 is illustrated as extending under the head support assembly 22, it will be apparent it may terminate at a front face 28 of the head support assembly 22 provided the assembly 22 is suitably thickened, i.e. the junction between the base 16 and the head support assembly 22 may be vertical rather than horizontal as illustrated.

The upper surface 30 of the head support assembly 22 is preferably horizontal but may tilt slightly to the rear and provides a pair of inclined sections 32, 34 adjacent the sides of the pillow 10 for purposes more fully apparent hereinafter.

The pillow 10 manifestly can be made of different size to accommodate larger or smaller individuals. An additional technique to this end is to provide a removable block 36 in the head support assembly 22. With the block 36 removed, there is a much shorter distance between the thoracic support assembly 20 and the surface that effectively supports the sleeper's head thereby providing a simple means to adjust the core 12 to accommodate smaller individuals.

Extending forwardly from the head support assembly 22 are a pair of arms or panels 38, 40 that merge with the base 16 or, more specifically, with the thoracic support assembly 20 and/or the waist and lumbar support assembly 18. The arms 38, 40 are spaced apart a distance smaller than the width of the sleeper's shoulders and larger than the thickness of the sleeper's torso, i.e. the distance from the inside faces of the arms 38, 40 are less than the width of the sleeper's shoulders and larger than the thickness of the sleeper's torso. Although the distance between the arms 38, 40 may vary somewhat, this distance is almost always eighteen inches or less. For a child's size pillow of this invention, the distance between the arms 38, 40 is typically less than one foot.

The arms 38, 40 may extend toward the waist and lumbar support assembly 18 for a suitable distance, which may vary considerably. It is preferred that the arms 38, 40 not be very long in order to minimize any claustrophobic sensations by the sleeper. The arms 38, 40 taper toward the waist and lumbar support assembly 18 as shown best in FIG. 1 and taper downwardly toward the thoracic support assembly 20 as shown best in FIG. 2.

Although the pillow 10 may be made with one arm 38, 40 on an edge of the pillow, FIG. 1 shows a preferred embodiment where both arms 38, 40 are spaced from the edges of the pillow 10 in order so the user can sleep on either side. Spacing the arms 38, 40 from the edges of the pillow 10 creates an area between the outside of the arm and the face 28 for the sleeper's arm to fit. A side ramp 42, 44 is placed between the outside of each arm 38, 40 and the face 28 to provide a rest for the forearm of the user. This is much more comfortable for the sleeper when compared to the situation where the forearm rests horizontally on the base 16. Each side ramp 42, 44 merges with the inclined sections 32, 34 of the head support assembly 22 thereby providing a long support section for the forearm and hand of the sleeper. The angle of the side ramps 42, 44 and the inclined sections 32, 34 are preferably equal to provide a long more-or-less continuous inclined section for receiving the forearm and hand of the sleeper.

In small batches, the pillow 10 is made by cutting and gluing blocks of foam material to provide the core 12 which is then covered with a soft foam cover 14. This approach is very similar to the manufacture of the pillow shown in U.S. Pat. No. 6,226,817, the disclosure of which is incorporated herein by reference. When larger production runs are feasible, a mold may be made in which to cast a complete pillow. In the alternative, the pillow 10 may be of an inflatable member which also provides a number of advantages. It will be seen that the foam cover 14 not only provides a desirable surface texture, it also modifies the shape of the underlying core 12 to the extent of providing a rounded pillow 10 as shown in FIG. 3 rather than the angular appearing core 12 as shown in FIGS. 1-2.

As shown in FIG. 1, if it is desirable to make a wedge shaped pillow in order to elevate the sleeper's head, a convenient technique is to make the base 16 of wedge shape or add one or more wedges 46 below the base 16. In the alternative, a mechanical adjustment may be provided on an underlying chaise lounge type support, as is common in outdoor furniture.

Use of the pillow 10 should now be apparent. The pillow 10 is typically covered with a pillow case. The sleeper lies on one side, e.g. the right side for purposes of illustration, with the head on the head support assembly 22 in the area of the block 36. It will be appreciated that the face of the sleeper, or rather the side of the face, is supported either on the top surface 30 of the head support assembly 22 or on a top surface 48, 50 of the arms 38, 40, depending on whether the sleeper is more-or-less straight or is somewhat curled. The sleeper's right shoulder lies in the corner between the thoracic support assembly 20 and the face 28 of the head support assembly 22. The sleeper's right arm, from the shoulder to the elbow, lies adjacent the sleeper's torso. The right arm of the sleeper can either be straight at the side of the sleeper or can bend at the elbow so the forearm lies on the side ramp 42 with the sleeper's right hand on the inclined section 32. Thus, the length of the arms 38, 40 is roughly the length of a sleeper's arm from the shoulder to the elbow, or shorter.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A method of using a pillow arranged to encourage a person to sleep on a side, comprising a head support assembly to receive and support the person's head and neck, the head support assembly being connected to a thoracic support assembly which is, in turn, connected to a waist and lumbar support assembly; the head support assembly extending generally perpendicularly upwardly from the thoracic support assembly to provide a shoulder receiving area between the thoracic support assembly and the head support assembly, the head support assembly extending laterally for a predetermined distance and terminating in first and second sides; a pair of arms merging with the thoracic support assembly and extending from the head support assembly toward the waist and lumbar support assembly, the arms being spaced apart a distance, not greater than eighteen inches, sufficient to receive a sleeper's torso when on a side and an insufficient distance to receive a sleeper's torso when the sleeper is supine, a first of the arms being spaced from a first side of the head support assembly to provide a space for an arm of the sleeper; and a side ramp inclined upwardly from the thoracic support assembly to the head support assembly providing an inclined position for the sleeper's arm, the method comprising:

measuring the shoulder width of the person;

preparing a pillow having dimensions such that the distance between the arms is less than the shoulder width of the person and sufficient to receive the person's torso when on a side and an insufficient distance to receive the person's torso when the sleeper is supine;

positioning the person, on a side between the arms, the person's shoulder width being greater than the distance between the arms, and allowing the person to go to sleep on a side.

2. A method of using a pillow arranged to encourage a person to sleep on a side, comprising a head support assembly to receive and support the person's head and neck, the head support assembly being connected to a thoracic support assembly which is, in turn, connected to a waist and lumbar support assembly; the head support assembly extending generally perpendicularly upwardly from the thoracic support assembly to provide a shoulder receiving area between the thoracic support assembly and the head support assembly, the head support assembly extending laterally for a predetermined distance and terminating in first and second sides; a pair of arms merging with the thoracic support assembly and extending from the head support assembly toward the waist and lumbar support assembly, the arms being spaced apart a distance, not greater than eighteen inches, sufficient to receive a sleeper's torso when on a side and an insufficient distance to receive a sleeper's torso when the sleeper is supine, a first of the arms being spaced from a first side of the head support assembly to provide a space for an arm of the sleeper; and a side ramp inclined upwardly from the thoracic support assembly to the head support assembly providing an inclined position for the sleeper's arm, the method comprising:

determining the shoulder width of the person, preparing a pillow having dimensions such that the distance between the arms is less than the shoulder width of the person and sufficient to receive the person's torso when on a side and an insufficient distance to receive the person's torso when the sleeper is supine;

delivering the pillow to the person, instructing the person to sleep on a side between the arms; and allowing the person to go to sleep on a side.

* * * * *